(12) United States Patent
Dai et al.

(10) Patent No.: US 11,345,934 B1
(45) Date of Patent: May 31, 2022

(54) METHOD FOR ANAEROBICALLY FERMENTING ORGANIC SOLID WASTE

(71) Applicant: TONGJI UNIVERSITY, Shanghai (CN)

(72) Inventors: Xiaohu Dai, Shanghai (CN); Yu Hua, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 17/565,169

(22) Filed: Dec. 29, 2021

(30) Foreign Application Priority Data

Jan. 4, 2021 (CN) .......................... 202110002289.0

(51) Int. Cl.
| | | |
|---|---|---|
| *C12P 1/00* | (2006.01) | |
| *C12P 39/00* | (2006.01) | |
| *C02F 11/122* | (2019.01) | |
| *C02F 11/127* | (2019.01) | |
| *C02F 11/04* | (2006.01) | |
| *C02F 103/00* | (2006.01) | |

(52) U.S. Cl.
CPC ................ *C12P 1/00* (2013.01); *C02F 11/04* (2013.01); *C02F 11/122* (2013.01); *C02F 11/127* (2013.01); *C12P 39/00* (2013.01); *C02F 2103/005* (2013.01)

(58) Field of Classification Search
CPC .. C12P 1/00; C12P 39/00; C02F 11/04; C02F 11/122; C02F 11/127; C02F 2103/005
USPC .......................................................... 435/42
See application file for complete search history.

(56) References Cited

U.S. PATENT DOCUMENTS

2008/0176301 A1* 7/2008 Granda .................... C12P 7/54
435/157

FOREIGN PATENT DOCUMENTS

| | | | |
|---|---|---|---|
| CN | 101337838 B | | 2/2012 |
| CN | 106244442 A | | 12/2016 |
| CN | 110194572 A | | 9/2019 |
| CN | 110964209 | * | 4/2020 |
| CN | 110964209 A | | 4/2020 |
| CN | 11826403 A | | 10/2020 |
| CN | 112111531 A | | 12/2020 |
| JP | S63214399 A | | 9/1988 |

OTHER PUBLICATIONS

He-Qi Zheng, Chun-Yan Liu, Xue-Yu Zheng, Jin Chen, Jian Lu, Rong-Guang Lin, Rong Cao, Zu-Jin Lin and Jin-Wei Su; MOF-808: A Metal-Organic Framework with Intrinsic Peroxidase-Like Catalytic Activity at Neutral pH for Colorimetric Biosensing; 2018; Department of Applied Chemistry, College of Life Science, Fujian Agriculture and Forestry University, Fuzhou, Fujian 350002, People's Republic of China.
Beatriz Villoria-Del-Álamo, Zr-MOF- 808 as Catalyst for Amide Esterification, Heterogeneous Cataly, nHeterogeneous Catalysis. 2020.

\* cited by examiner

*Primary Examiner* — Jennifer M. H. Tichy

(57) ABSTRACT

Provided herein is a method for anaerobically fermenting an organic solid waste, including: subjecting the organic solid waste to anaerobic fermentation under catalysis of a zirconium-based metal organic framework (MOF) material.

6 Claims, 1 Drawing Sheet

METHOD FOR ANAEROBICALLY FERMENTING ORGANIC SOLID WASTE

CROSS-REFERENCE TO RELATED APPLICATIONS

This application claims the benefit of priority from Chinese Patent Application No. 202110002289.0, filed on Jan. 4, 2021. The content of the aforementioned application, including any intervening amendments thereto, is incorporated herein by reference in its entirety.

TECHNICAL FIELD

This application relates to anaerobic fermentation, and more specifically to a method for anaerobically fermenting an organic solid waste.

BACKGROUND

The organic solid waste mainly includes domestic waste (e.g., urban sludge, domestic garbage and garden waste), agricultural waste (e.g., straw, mulching film, and livestock and poultry manure) and industrial waste (e.g., oil sludge, medicine residue and bacterial residue). More than 6 billion tons of the organic solid waste are produced annually, accounting for more than 60% of a total production of the solid waste. However, there is still a lack of a scientific and reasonable management method for safely treating the organic solid waste. The organic solid waste will cause typical pollution, and has complex components and many harmful media. Moreover, it will also leads to multi-phase combined cross-contamination with a surrounding environment during the stockpiling. Therefore, it is necessary to develop a reasonable and scientific method for harmlessly treating the organic solid waste.

In view of the high organic content and perishable characteristic of the organic solid waste, the anaerobic digestion strategy is considered to be a promising tool in the treatment of the organic solid waste. Anaerobic digestion can not only reduce the amount of the organic solid waste, but also produce biogas as an energy source, simultaneously achieving the energy recycling and environmental and ecological protection. Organic substances can be converted into an ideal clean energy methane with a high heat value (802.3 kJ/mol) through anaerobic fermentation driven by an anaerobic microorganism. However, most of organic solid wastes have poor biodegradability, which will render the anaerobic digestion time-consuming. Generally, a 20-30-day anaerobic digestion can only reach a moderate degree of degradation (about 30-50%). The residence time of the organic solid waste in a digestion system is too long, resulting in large space occupation and complicated operation and management. Extensive researches have been conducted on the introduction of pretreatment to promote the anaerobic fermentation of the organic solid waste, such as addition of acid or alkali, heat treatment and microwave-assisted treatment. Unfortunately, these methods generally struggles with high cost and considerable energy consumption, and thus are not suitable for the practical application. Therefore, it is urgently needed for those skilled in the art to develop a cost-effective and industrially-applicable method to promote the sludge anaerobic fermentation.

SUMMARY

In order to solve the above technical problems, the present disclosure provides a method for anaerobically fermenting an organic solid waste, in which a zirconium-based metal-organic framework (MOF) material is employed as a catalyst to promote the liquefaction and decomposition of the organic solid waste, and improve the methane production capacity and efficiency.

Technical solutions of this application are described as follows.

Provided herein is a method for anaerobically fermenting an organic solid waste, comprising:

subjecting the organic solid waste to anaerobic fermentation under catalysis of a zirconium-based MOF material.

In an embodiment, the zirconium-based MOF material is MOF-808 (Zr); and the organic solid waste is wet waste, a sludge from a sewage treatment plant, an agricultural straw, a bacterial residue or a combination thereof.

MOF-808 (Zr) has an MTN topological structure with two different cages, in which a hexazirconium cluster as a secondary building unit is bridged to trimesic acid as an organic ligand to form a supertetrahedral structure, which is connected with the organic ligand to continuously extend in the three-dimensional space. As a highly-active site in the structure, the metal oxide cluster or organic ligand also has a high catalytic activity in a neutral environment (the anaerobic fermentation process is generally performed under a neutral or slightly alkaline environment). Moreover, the porosity and the large specific surface area of the MOF-808 (Zr) material help reactants diffuse into the active sites to participate in the catalytic reaction, and facilitate the rapid discharge of reaction products. Simultaneously, the above characteristics also facilitate accelerating the biological reactions involved in the anaerobic digestion, promoting the liquefaction and decomposition of the organic solid waste, and improving the methane production capacity and efficiency.

In an embodiment, the zirconium-based MOF material is applied in a powder form, in a compression molded material form, or by forming a MOF-808 film on an inner wall of a reactor through a secondary growth method.

In an embodiment, the step of "subjecting the organic solid waste to anaerobic fermentation under catalysis of a zirconium-based MOF material" comprises:

blending the organic solid waste, an anaerobic microorganism and the zirconium-based MOF material uniformly to obtain a mixture; and subjecting the mixture to a closed anaerobic fermentation in an anaerobic fermentation tank to collect biogas produced during the closed anaerobic fermentation.

In an embodiment, a weight ratio of the organic solid waste to the anaerobic microorganism is (0.5-2):1; an addition amount of the zirconium-based MOF material is 0.5 g/L; and a solid content of the mixture is less than 10%.

In an embodiment, the anaerobic microorganism is derived from a biogas residue discharged from the anaerobic fermentation tank.

In an embodiment, in an initial operation of the anaerobic fermentation tank, the anaerobic microorganism is a sludge from an anaerobic fermentation tank of a sewage treatment plant or an animal rumen fluid.

In an embodiment, the closed anaerobic fermentation is performed at 37-55° C. under stirring at 80 rpm for 30 days.

In an embodiment, an anaerobic fermentation residue obtained after the closed anaerobic fermentation is subjected to slurry-water separation to collect a biogas residue as an inoculation microorganism for subsequent anaerobic fermentation.

In an embodiment, the slurry-water separation is performed by 12-h standing, centrifugal dewatering or plate-frame filter pressing.

Compared to the prior art, the present disclosure has the following beneficial effects.

The present disclosure improves an efficiency of anaerobic fermentation and an output of methane by introducing the zirconium-based MOF material in the anaerobic fermentation process, which is beneficial to the reduction of the organic solid waste. The biogas residue generated from the fermentation contains a large amount of nitrogen, phosphorus and other trace elements, and can be recycled or used as a fertilizer for the agricultural production. The method provided herein has low operation and maintenance cost, simple operation, and strong processing capacity, and can be applied to newly-built equipment for anaerobic fermentation of the organic solid waste or the upgradation and transformation of existing equipment.

After the organic solid waste is treated by the anaerobic fermentation method provided herein, three kinds of products are generated, including biogas, biogas slurry and biogas residue, where the biogas is a clean energy; and the biogas slurry and the biogas residue can be used as a fertilizer. The introduction of the zirconium-based MOF material can improve the yield and production efficiency of biogas.

Figure 1:
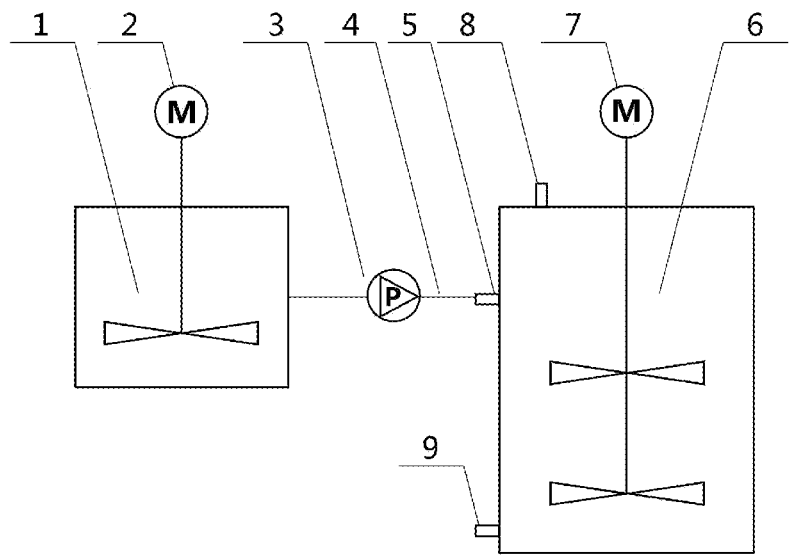
FIG. 1 schematically illustrates a structure of a system for zirconium-based MOF material-catalyzed anaerobic fermentation of an organic solid waste according to Example 1 of the present disclosure.

In the drawings: 1, mixing tank; 2, first stirring system; 3, delivery pump; 4, pipeline; 5, feeding port; 6, anaerobic fermentation tank; 7, second stirring system; 8, gas outlet; and 9, mud discharge port.

DETAILED DESCRIPTION OF EMBODIMENTS

The disclosure will be described completely and clearly below with reference to the accompanying drawings and embodiments to make the object, technical solutions, and beneficial effects of the present disclosure clearer. The embodiments provided herein are merely illustrative, and are not intended to limit the scope of the present disclosure.

It should be understood that the terms used herein are only used to describe specific embodiments and are not intend to limit the present disclosure. In addition, as used herein, the numerical range contains any intermediate value between the upper limit and the lower limit of the range. Each smaller range between any stated value or intermediate value within the stated range and any other stated value or intermediate value within the stated range also fall into the scope of the present disclosure. The upper and lower limits of these smaller ranges can be independently included or excluded from the range.

Unless otherwise stated, all technical and scientific terms used herein have the same meaning as commonly understood by those skilled in the art. Although the present disclosure only describes preferred methods and materials, any methods and materials similar or equivalent to those described herein can also be used in the implementation or test of the present disclosure. All documents mentioned herein are incorporated by reference to disclose and describe methods and/or materials related to the documents.

It should be understood that various improvements and changes made by those skilled in the art without departing from the scope and spirit of the present disclosure shall fall within the scope of the disclosure.

As used herein, terms "comprise", "include", "have" and "contain" all represent a non-exclusive inclusion, which means "including but not limited to".

Example 1

FIG. 1 depicts a schematic structural diagram of anaerobic fermentation of an organic solid waste under catalysis of a zirconium-based metal-organic framework (MOF) material in Example 1, where 1, mixing tank; 2, first stirring system; 3, delivery pump; 4, pipeline; 5, feeding port; 6, anaerobic fermentation tank; 7, second stirring system; 8, gas outlet; and 9, mud discharge port.

The method includes the following steps.

(S1) Preparation of MOF-808 (Zr)

Trimesic acid and zirconium chloride tetrahydrate were weighed to dissolve in a flask containing N,N-dimethylamide/formic acid (volume ratio 1:1), and stirred for 1 h, and then a mixed solution obtained was microwaved at 400 KW for 20 min, and cooled to room temperature to obtain an solid. The solid was filtered, washed, dried, and grounded to obtain a MOF-808 (Zr) powder. In which, a molar ratio of the trimellitic acid to the zirconium chloride tetrahydrate was 1:2.

A chemical formula of the MOF-808 (Zr) was $Zr_6O_5(OH)_3(BTC)_2(HCOO)_5(H_2O)_2$, and the MOF-808 has a particle diameter of 1-1.5 μm, a pore size of 14-18 Å and a specific surface area of $1000\pm200$ m$^2$/g.

(S2) Anaerobic Fermentation

The organic solid waste (wet waste) to be treated and an anaerobic microorganism (a sludge from an anaerobic fermentation tank of a sewage treatment plant) were added to the mixing tank 1 according to a weight ratio of 1:2, and 0.5 g/L of the MOF-808 (Zr) powder was added to the mixing tank 1. The first stirring system 2 was turned on to stir the organic solid waste to be treated, the MOF-808 (Zr) powder and the anaerobic microorganism uniformly, and water was added to adjust a solid content in the mixing tank 1 to be less than 10% to obtain a mixture. The delivery pump 3 was turned on, and the mixture was injected into the anaerobic fermentation tank 6 through the pipeline 4 through the feeding port 5. The mixture was subjected to a closed anaerobic fermentation in the anaerobic fermentation tank 6 at 50-55° C. for 30 days. The second stirring system 7 of the anaerobic fermentation tank with a stirring rate of 80 rpm was arranged on a top of the anaerobic fermentation tank 6 to fully mix the mixture in the anaerobic fermentation tank 6. The gas outlet 8 was arranged on an upper part of the anaerobic fermentation tank 6 for collecting biogas and detecting the biogas during the closed anaerobic fermentation.

(S3): An anaerobic fermentation residue obtained after the closed anaerobic fermentation was discharged through the mud discharge port 9, and subjected to slurry-water separation to collect a biogas residue as an inoculation microorganism for subsequent anaerobic fermentation. The slurry-water separation is performed by 12-h standing.

Comparative Example 1

Same as Example 1, the difference is that a MOF-808 (Zr) powder is not added in anaerobic fermentation.

Figure 2:
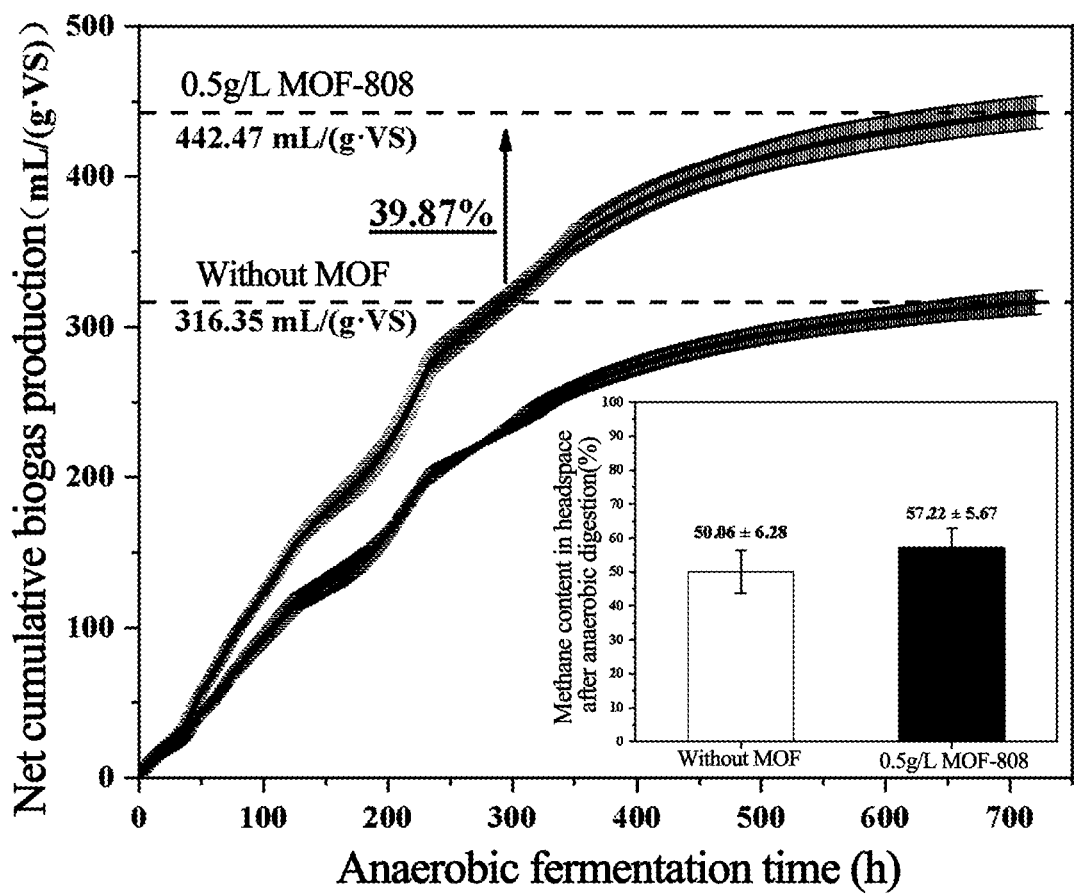
FIG. 2 illustrates comparison of biogas production between the anaerobic fermentation in the presence of the zirconium-based MOF material (Example 1) and the anaerobic fermentation in the absence of the zirconium-based MOF material (Comparative Example 1).

FIG. 2 illustrates comparison of biogas production between the anaerobic fermentation in the presence of the zirconium-based MOF material (Example 1) and the anaerobic fermentation in the absence of the zirconium-based MOF material (Comparative Example 1).

It can be clearly seen from FIG. 2 that after adding 0.5 g/L of the zirconium-based MOF material in the anaerobic fermentation, the net cumulative biogas production is 442.47 mL (g·VS) after anaerobic fermentation for 700 h, and a methane content in a headspace after anaerobic digestion is 57.77±5.67; the net cumulative biogas production after anaerobic fermentation without MOF for 700 h is 316.35 mL (g·VS), and a methane content in a headspace after anaerobic digestion is 50.06±6.28. Therefore, the zirconium-based MOF material can significantly improve an efficiency of anaerobic fermentation and increase a production of biogas. The zirconium-based MOF material with biocompatibility is an ideal catalyst to replace biological enzymes. The selected zirconium-based MOF material MOF-808 (Zr) is a rare type of MOFs material that has a high catalytic activity in neutral environment. The MOF-808 (Zr) material in the system catalyzes and accelerates a biological reaction process of anaerobic digestion, which can promote a liquefaction process and a decomposition process of the organic solid waste, and simultaneously promote a methane production activity, increase a methane production and a gas production rate.

Described above are only preferred embodiments of the present disclosure and are not intended to limit the present disclosure. It should be understood that any modifications, replacements and improvements made by those skilled in the art without departing from the spirit and scope of the present disclosure should fall within the scope of the present disclosure defined by the appended claims.

What is claimed is:

1. A method for anaerobically fermenting an organic solid waste, comprising:

blending the organic solid waste, an anaerobic microorganism and a zirconium-based metal-organic framework (MOF) material uniformly to obtain a mixture; and subjecting the mixture to a closed anaerobic fermentation in an anaerobic fermentation tank to collect biogas produced during the closed anaerobic fermentation;

wherein a weight ratio of the organic solid waste to the anaerobic microorganism is 0.5-2:1; an amount of the zirconium-based MOF material is 0.5 g/L; and a solid content of the mixture is less than 10%; and the zirconium-based MOF material is MOF-808 Zr; and the organic solid waste is wet waste, a sludge from a sewage treatment plant, an agricultural straw, a bacterial residue or a combination thereof.

2. The method of claim 1, wherein the anaerobic microorganism is derived from a biogas residue discharged from the anaerobic fermentation tank.

3. The method of claim 1, wherein in an initial operation of the anaerobic fermentation tank, the anaerobic microorganism is a sludge from an anaerobic fermentation tank of a sewage treatment plant or an animal rumen fluid.

4. The method of claim 1, wherein the closed anaerobic fermentation is performed at 37-55° C. under stirring at 80 rpm for 30 days.

5. The method of claim 1, wherein an anaerobic fermentation residue obtained after ending the anaerobic fermentation is subjected to slurry-water separation to collect a biogas residue as an inoculation microorganism for subsequent anaerobic fermentation.

6. The method of claim 5, wherein the slurry-water separation is performed by standing for 12 hours, centrifugal dewatering or plate-frame filter pressing.

* * * * *